(12) United States Patent
Rikimaru

(10) Patent No.: US 7,729,907 B2
(45) Date of Patent: Jun. 1, 2010

(54) APPARATUS AND METHOD FOR PREVENTING SENILITY

(75) Inventor: Hiroshi Rikimaru, 1-7-12-505, Higashihiraki-cho, Takano, Sakyo-ku, Kyoto-shi, Kyoto (JP) 606-8107

(73) Assignees: Rion Co., Ltd., Tokyo (JP); Hiroshi Rikimaru, Kyoto (JP)

( * ) Notice: Subject to any disclaimer, the term of this patent is extended or adjusted under 35 U.S.C. 154(b) by 1016 days.

(21) Appl. No.: 10/583,717

(22) PCT Filed: Feb. 21, 2005

(86) PCT No.: PCT/JP2005/002695

§ 371 (c)(1),
(2), (4) Date: Jun. 20, 2006

(87) PCT Pub. No.: WO2005/087301

PCT Pub. Date: Sep. 22, 2005

(65) Prior Publication Data

US 2007/0185710 A1    Aug. 9, 2007

(30) Foreign Application Priority Data

Mar. 11, 2004    (JP) .............................. 2004-068842

(51) Int. Cl.
*G10L 21/00* (2006.01)
(52) U.S. Cl. ...................... 704/228; 704/226; 704/271; 704/274; 434/185
(58) Field of Classification Search ......... 704/226–228, 704/270–275; 434/185
See application file for complete search history.

(56) References Cited

U.S. PATENT DOCUMENTS 3,784,750 A    1/1974   Stearns et al.
4,989,248 A *  1/1991   Schalk et al. ............... 704/252

(Continued)

FOREIGN PATENT DOCUMENTS

CN         137666 A    12/1986

(Continued)

OTHER PUBLICATIONS

Robert V. Shannon et al., "Speech Recognition with Primarily Temporal Cues", Science, New Series. vol. 270, pp. 303-304, House Ear Institute, (Oct. 1995).

(Continued)

*Primary Examiner*—Vijay B Chawan
(74) *Attorney, Agent, or Firm*—Rader, Fishman & Grauer PLLC

(57) ABSTRACT

Preparing for the full-fledged aged society, measures to prevent senility are required. Senility is prevented by extracting signals of prescribed bands from a speech signal using a first bandpass filter section having a plurality of bandpass filters, extracting the envelopes of each frequency band signal using an envelope extraction section having envelope extractors, applying a noise source signal to a second bandpass filter section having a plurality of bandpass filters and extracting noise signals corresponding to the prescribed bands, multiplying the outputs from the first bandpass filter section and the second bandpass filter section in a multiplication section, summing up the outputs from the multiplication section in an addition section to produce a Noise-Vocoded Speech Sound signal, and presenting the Noise-Vocoded Speech Sound signal for listening.

8 Claims, 8 Drawing Sheets

U.S. PATENT DOCUMENTS

| | | | |
|---|---|---|---|
| 5,303,327 A * | 4/1994 | Sturner et al. | 704/270 |
| 5,356,287 A | 10/1994 | McIntyre | |
| 5,456,606 A | 10/1995 | McIntyre | |
| 5,754,978 A * | 5/1998 | Perez-Mendez et al. | 704/255 |
| 5,794,188 A * | 8/1998 | Hollier | 704/228 |
| 6,109,107 A * | 8/2000 | Wright et al. | 73/585 |
| 6,708,154 B2 * | 3/2004 | Acero | 704/260 |
| 6,970,570 B2 * | 11/2005 | Goldstein | 381/321 |
| 7,110,951 B1 * | 9/2006 | Lemelson et al. | 704/270 |
| 7,203,643 B2 * | 4/2007 | Garudadri | 704/233 |
| 2005/0069162 A1 * | 3/2005 | Haykin et al. | 381/312 |

FOREIGN PATENT DOCUMENTS

| | | |
|---|---|---|
| CN | 1452110 A | 10/2003 |
| JP | 06-070981 A | 3/1994 |
| JP | 10-244003 A | 9/1998 |
| JP | 2003-107983 A | 4/2003 |

OTHER PUBLICATIONS

Translation of Office Action 200580001572.0 issue dated Dec. 5, 2008.

Shannon et al., "Speech Recognition with Primarily Temporary Cues," Science, vol. 270, (Oct. 1995).

Obata, "Speech Perception Based on Temporal Amplitude Change with Spectrally Degraded Synthetic Sound," Transactions of the Technical Committee on Psychological and Physiological Acoustics, H-99-6, Acoustical Society of Japan, (Jan. 1999).

Obata, "Intelligibility of Synthesized Japanese Speech Sound Made of Band Noise," Trans. Tech. Comm. Psychol. Physiol. Acoust., H-2000-3, The Acoustical Society of Japan, (Jan. 2000).

International Search Report.

* cited by examiner

US 7,729,907 B2

APPARATUS AND METHOD FOR PREVENTING SENILITY

TECHNICAL FIELD

The present invention relates to apparatuses and methods for preventing senility that prevent senility by enhancing brain activity through listening to Noise-Vocoded Speech Sound produced by subjecting frequency band signals to noise degradation in at least a portion of a speech signal.

BACKGROUND ART

It is known from past research into speech signal recognition that even if a subject hears a speech signal not "as is" and components of the speech signal are subjected to noise degradation using a predetermined method, words can still be recognized to a considerable extent. For example, such technology has been described in non-patent document 1, non-patent document 2, and non-patent document 3.

According to the documents, a signal is produced by summing up signals produced by dividing a speech signal into 4 frequency bands (0-600, 600-1500, 1500-2500, and 2500-4000 Hz), obtaining amplitude envelopes for each frequency band by subjecting the respective speech signals to half-wave rectification and low-pass filtering at 16 Hz, and overlaying the envelopes on band noise corresponding to each frequency band. Such a signal is called Noise-Vocoded Speech Sound. An intelligibility of about 80% has been reported when presenting normal-hearing subjects with Noise-Vocoded Speech Sound.

[Non-patent document 1] Shannon, R. V., et al.: "Speech Recognition with Primarily Temporal Cues", Science, Vol. 270, pp. 303-305 (1995)

[Non-patent document 2] Yoshihisa Obata, Hiroshi Riquimaroux: Speech perception based on temporal amplitude change with spectrally degraded synthetic sound, Materials of the Auditory Research Forum of The Acoustical Society of Japan, H-99-6 (1999).

[Non-patent document 3] Yoshihisa Obata, Hiroshi Riquimaroux: Intelligibility of synthesized Japanese speech sound made of band noise—preliminary study for a speech recognition processor utilizing central auditory function—, Materials of the Auditory Research Forum of The Acoustical Society of Japan, H-2000-3 (2000).

DISCLOSURE OF THE INVENTION

Problems to be Solved by the Invention

In recent years, there is a growing concern that the number of the aged people who suffer from senility will increase along with aging of the society. While various opinions have been presented concerning prevention of senility, for example, to keep interests in his/her surroundings such as the society in his/her daily life, or to have regular conversation with his/her friends or family members, no effective preventive method has been established yet. Methods and apparatuses that can prevent senility effectively will be helpful in the coming full-fledged aged society.

Means for Solving the Problems

To solve the problem, the following means and procedures have been adopted in the inventive apparatus and method for preventing senility.

(1) Generating and constructing a Noise-Vocoded Speech Sound signal by dividing at least a portion of an input speech signal into a single frequency band signal or a plurality of frequency band signals and subjecting the single frequency band signal or the plurality of frequency band signals to noise degradation, with the generated Noise-Vocoded Speech Sound signal presented for listening to a user.

(2) Producing a Noise-Vocoded Speech Sound signal whose speech source signal component is subjected to noise degradation by extracting signals of prescribed bands from a speech signal using a first bandpass filter section having a plurality of bandpass filters, extracting the envelopes of each frequency band signal using an envelope extraction section having envelope extractors, applying a noise source signal to a second bandpass filter section having a plurality of bandpass filters and extracting noise signals corresponding to the prescribed bands, multiplying the outputs from the envelope extraction section and those from the second bandpass filter section in a multiplication section, and summing up the outputs from the multiplication section in an addition section.

(3) Enabling selection or modification of the number of the bandpass filters and the frequency boundaries of the bands. By selecting or modifying the number of the bandpass filters and the frequency boundaries of the bands that are suited for the relevant language through automatic language recognition, the apparatuses and methods for preventing senility can be used by people having a plurality of nationalities, and can be used to prevent senility among foreign people as well.

(4) Since the method for preventing senility can be implemented as a procedure in the form of a computer program or the like, it may be provided as a software program storing medium, on which a program to be executed on a computer is stored, or as a software program to be executed on a computer.

EFFECT OF THE INVENTION

With the present invention, it is possible to activate brain by apparatuses and methods for preventing senility in which normal speech is converted into Noise-Vocoded Speech Sound to enhance brain functions and facilitate language comprehension, and accordingly prevent a cause of senility from occurring in brain. Therefore, effect of preventing appearance of senility symptoms can be expected.

BEST MODE FOR CARRYING OUT THE INVENTION

Below, embodiments of an apparatus and so on for preventing senility are explained by referring to drawings. It should be noted that duplicate explanations have been omitted in some cases because components assigned the same numerals in the embodiments perform similar operations.

Embodiment 1

FIG. 1 is a block diagram of an apparatus for preventing senility of the present invention. In FIG. 1, an input speech signal recorded through a microphone is applied to a bandpass filter section 1 via an input terminal 7. The bandpass filter section 1 has a plurality of bandpass filters 1a, 1b, 1c, and 1d, which extract signals of predetermined bands. The output signals of the bandpass filters 1a, 1b, 1c, and 1d are applied, respectively, to envelope extractors 2a, 2b, 2c, and 2d of an envelope extraction section 2. The envelope extractors 2a, 2b, 2c, and 2d respectively extract the envelopes of the frequency band signals. A noise signal outputted by a noise source 5 is applied to a bandpass filter section 4, which has a plurality of bandpass filters 4a, 4b, 4c, and 4d, and is divided into noise signals of the same frequency bands as the bandpass filter section 1. In a multiplication section 3, which has multipliers 3a, 3b, 3c, and 3d, the outputs of the envelope extractors 2a, 2b, 2c, and 2d and those of the bandpass filters 4a, 4b, 4c, and 4d are multiplied together for each corresponding frequency band. The plurality of multiplication results are added up in an addition section 6 and output as an output signal at an output terminal 8. It should be noted that the bandpass filters possess the well-known function of extracting predetermined frequency components from a signal and can be composed of analog circuits, digital circuits, digital signal processors, etc. Furthermore, the envelope extractors possess the well-known function of detecting variation in the amplitude value of a signal and can be composed of analog circuits, digital circuits, digital signal processors, etc. based on the principles of half wave rectification and full-wave rectification. Moreover, in the bandpass filter sections 1 and 4, high pass filters may be used for the bandpass filters 1a and 4a that process the highest bands. Low pass filters may be used as the bandpass filters 1d and 4d that process the lowest bands.

It has been found that presenting the thus produced Noise-Vocoded Speech Sound for listening through earphones results in the activation of various regions other than the regions typically activated during aural recognition in the brain. When the activated brain regions are examined using an MRI device while presenting the above-described four-band Noise-Vocoded Speech Sound for listening, activation is observed in the regions of the left temporal lobe that are believed to be used for regular speech recognition. Also, in addition to that, activation is observed in regions believed to be related to functions other than speech recognition, such as the right temporal lobe, the frontal lobe, the parietal lobe, the right side of the cerebellum, etc. FIG. 8 illustrates the results of observation of brain activation using a functional MRI device. The regions shown in white are the regions, in which above-baseline activation was observed. In FIG. 8, Sub.A, Sub.B, and Sub.C indicate subjects. B4, B1, N, and S are the presented stimuli, which are, respectively, as follows. B4 was produced by dividing speech material into four frequency bands using bandpass filters, extracting the respective amplitude envelopes, setting the boundary frequencies to 600, 1500, and 2100 Hz, and overlaying the amplitude envelopes on narrowband noise of the corresponding frequency bands. B1 was obtained by extracting the amplitude envelope for all the frequency bands and overlaying it on the noise. However, in such noise, the effective values of the speech material, divided using the boundary frequencies, are applied to the corresponding bands in advance. S represents speech material used "as is". N represents an approximation of the power spectrum to B4 using the same method as in the case of B1, but without imposing the amplitude envelopes. Speech material was obtained by recording simple sentences consisting of 12 to 16 moras (2 to 3 seconds) using a sampling frequency of 8000 Hz and a quantization accuracy of 16 bits. In addition, low frequency noise (40 Hz or less) in the material was reduced using a high-pass filter. [B4-B1] in FIG. 8 illustrates the difference in the activity of stimulus B4 and stimulus B1. The activated regions in the left temporal lobe observed in [S-N] (FIG. 8c) are believed to be the regions used for regular speech recognition. The same regions as in [S-N] are activated in [B4-B1] (FIGS. 8a, 8b) and in [B4-N] (FIG. 8e). Moreover, in addition to that, activation can be seen in the right temporal lobe as well. In addition, activation can be seen on both sides of the frontal lobe in Sub.B, and on both sides of the frontal lobe and parietal lobe, as well as on the right side of the cerebellum in Sub.C. Based on this, it is reasonable to believe that, during listening to B4, speech recognition is carried out using other ancillary processing means in addition to regular speech recognition processing. Moreover, considerable cross-subject variation is observed in terms of activation patterns other than those of the temporal lobes, and it is believed that there are individual differences in the activation of regions other than the regular speech recognition regions. Therefore, there is a chance that regions may be activated that were not expected to be artificially activated in the past.

Because the activation of brain activity maintains and enhances the functions of its regions, quite naturally, it can prevent impairment of the functions of the regions responsible for aural recognition and, in addition, for various regions other than the regions responsible for aural recognition, one can expect effects in preventing senility. Usually, it is not easy for an ordinary person to selectively activate a specific region of the brain. In addition, there are regions that cannot be activated without special mental activities and training. In accordance with the present invention, since various brain regions can be activated subconsciously, the invention is effective in preventing senility. Here, "senility" refers to a condition in which intelligence once acquired is continuously lost, namely, dementia.

Further, the Noise-Vocoded Speech Sound is expected to activate the brain activity in regions subject to brain damage that is considered to cause senility. Therefore, other than reinforcement of aural function, one can expect prevention of occurrence of senility phenomena or relief of senility symptoms due to recovery of functions in damaged brain regions.

Next, a modification of the apparatus for preventing senility is described. For example, in case of a hearing-impaired person who has a low sensitivity for a certain frequency band, the respective bandpass filters can be provided with frequency characteristics that compensate such a characteristic of low sensitivity for that certain frequency band. When an audible volume range of a subject is limited, if listening in a small volume is difficult for the subject, and also in a large volume, presented speech is too distorted for the subject to aurally comprehend, non-linear multiplication characteristics can be provided to the multipliers 3a, 3b, 3c and 3d of the multiplication section 3 so as to correct the dynamic range of the presented speech as appropriate. Provision of characteristics to compensate hearing disability that is common to the aged people facilitates their language comprehension, and further activates brain activity.

As explained above, the band noise signals were produced by a noise source 5. However, they can also be produced by subjecting a speech signal to distortion and noise degradation. The input signal of the bandpass filter section 1 may be subjected to distortion; otherwise, the output signals of the bandpass filters 1a to 1d may be distorted for use.

In FIG. 1, the respective envelopes of the speech signals in four different frequency bands were detected and the amplitude of the corresponding band noise signals was modulated in accordance with the envelope signals; however, it is also possible to use only some of the envelope signals. As for the rate, with which the envelope signals change over time, it is possible to use envelope signals that follow the speech variations closely or signals that change more slowly. That is, it is possible to use the time-series mean of the envelope signal for each frequency band. In addition, an envelope signal obtained from all the frequency bands can be used as well. Although the brain activation effects may be somewhat weaker, activation can also be achieved in regions other than the aural recognition and speech recognition regions.

Although in FIG. 1 all the speech signals belonging to the four frequency bands were replaced with band noise signals, residual speech signal components may be allowed by applying the speech signals from some of the frequency bands to the adder 6 directly, without applying them to the multiplication section 3. With respect to the frequency bands with residual speech signal components, appropriate correction may be performed according to frequency characteristics or degradation of the dynamic range of the relevant hearing disability.

According to the present embodiment, as described above, there is provided an apparatus for preventing senility, in which the user is presented with a Noise-Vocoded Speech Sound signal for listening obtained by dividing at least a portion of an input speech signal into a single frequency band signal or a plurality of frequency band signals and subjecting the frequency band signal or the frequency band signals to noise degradation. The use of the apparatus for preventing senility helps brain activation, and effects are expected in terms of preventing senility.

Embodiment 2

FIG. 2 is a block diagram of a game-like apparatus for preventing senility based on the use of Noise-Vocoded Speech Sound of the present invention. In FIG. 2, the bandpass filter section 1, the envelope extraction section 2, the multiplication section 3, the bandpass filter section 4, the noise source 5, and the addition section 6 are configured in the same manner as in FIG. 1. Speech signals made up of words and sentences are stored in a speech source signal section 10. A speech source selection control section 11 provides a control signal to the speech source signal section 10 in order to select and specify a speech signal of predetermined words and sentences. The speech source signal section 10 outputs the speech signal made up of the words and sentences specified by the speech source selection control section 11 to the bandpass filter section 1. A Noise-Vocoded Speech Sound signal made up of these words and sentences is output from the output terminal 8. It is presented to the user for listening through a speaker or headphones that is an output section for outputting the Noise-Vocoded Speech Sound signal. The instructor operates the speech source selection control section 11 in accordance with a program for preventing senility, and successively presents to the user words and sentences for listening. The users, upon listening to the Noise-Vocoded Speech Sound, orally convey the recognized words and sentences to the instructor. The instructor, upon evaluation of the correctness of their responses, informs the users of the results and moves on to the next step. The user's learning is based on information on correct and wrong responses. Depending on the correctness of the response, the instructor selects the subsequent words and sentences.

The standard frequency bands for the bandpass filters of the bandpass filter sections 1 and 4 are 0-600 Hz, 600-1500 Hz, 1500-2500 Hz, and 2500-4000 Hz. A band selection section 12 can switch the frequency bands of the bandpass filter sections 1 and 4. For instance, the number of frequency bands can be selected from 1, 2, 3, or 4. This is because, depending on the language, for example, for vowels, consonants, plosives, etc., there may be cases in which there is no need to have four frequency bands. For instance, by setting the output of the bandpass filters 1c, 1d, 4c, and 4d to zero, the number of frequency bands can be set to 2. Moreover, the boundary frequencies between the frequency bands for all or some of the bandpass filters can be switched and set to frequencies other than 600 Hz, 1500 Hz, 2500 Hz, and 4000 Hz. The values of 600 Hz, 1500 Hz, 2500 Hz, and 4000 Hz are close to the standard frequency boundaries separating vowels in speech, /a/, /i/, /u/, /e/, and /o/ in Japanese language at the first and second format. However, sometimes these frequency boundaries may vary depending on the person. Because the efficiency of preventing senility is expected to improve if the frequency band boundaries are adjusted and corrected in accordance with such individual differences, the boundary frequencies are made switchable. In addition, since the vowel system of a foreign language, that is, languages other than Japanese, may be different from that of Japanese, the number of bandpass filters and boundary frequencies can be made switchable so as to match the foreign language.

To accommodate a foreign language, an automatic language recognition section may be provided to automatically recognize the words and sentences initially inputted by the user and the instructor through the microphone. The country name data obtained as a result of the recognition by the automatic language recognition section may be supplied to the band selection section 12, with the band selection section 12 setting the number of bandpass filters and the frequency band boundaries in the bandpass filter sections 1 and 4 in accordance with the language of the specified country.

It should be noted that the selection and switching of the number of bandpass filters and the frequency band boundaries, as well as the selection and switching of the number of bandpass filters and the frequency band boundaries based on automatic language recognition, as described above is also applicable to the apparatus for preventing senility described in Embodiment 1.

As mentioned above, the effects of the game-like apparatus for preventing senility described in this embodiment consist in the enhancement of brain activity.

Embodiment 3

FIG. 3 is a block diagram of another embodiment of a game-like apparatus for preventing senility using the Noise-Vocoded Speech Sound of the present invention. This block diagram is described only for a portion different from FIG. 2. The Noise-Vocoded Speech Sound output from the addition section 6 is presented to the user for listening via the headphones 13 that is an output section. The speech source selection control section 11 also has a display signal generation control function in addition to the speech source signal selection function, and display in characters instructions to the user or correct responses of words and sentences in the Noise-Vocoded Speech Sound on the screen of a display device 14 that is a display section. A response input section 15 is a keyboard for inputting recognized words and sentences. Information signal from the response input section 15 is transmitted to the speech source selection control section 11, and the speech source selection control section 11 analyzes the response and selects the subsequent words and sentences to be presented based on the result of correctness of the response.

A software program for preventing senility is installed on the speech source selection control section 11. For example, ten basic words and sentences collected to form one group are successively presented to the user one by one, and the user, listening to the Noise-Vocoded Speech Sound of the words and sentences, inputs recognized responses in kana characters (Japanese syllabary) to the response input section 15. The speech source selection control section 11 compares the information signal indicating the response received by the response input section 15 with the text information corresponding to the words and sentences presented for listening through the headphones 13 in the timing in which the response is input to the response input section 15, and determines the correctness of the response. The speech source selection control section 11 then counts the number of correct and wrong responses, and at the same time display the determination result of correctness of the response or the correct response. If the response is correct, it is not required to display the correct response. After that, the speech source selection control section 11 controls the speech signal section 10 to present the subsequent Noise-Vocoded Speech Sound. The speech source selection control section 11 repeats this operation until presentation of all the ten words and sentences is finished. When presentation of, and providing responses to the ten words and sentences are finished, the speech source selection control section 11 displays the correct response percentage obtained by dividing the number of the counted correct responses by ten on the display device 14. In this way, the speech source selection control section 11 and the display device 14 perform a function as a correctness output section that outputs correctness of responses. Finally, the speech source selection section 11 may present the ten tasks again for letting the user confirm the tasks. In this way, users can learn for themselves without the instructor. The speech source selection control section 11 then starts a task program of an appropriate difficulty level according to the correct response percentage. For example, if the correct response percentage is 50% or more, a task program whose difficulty level is higher than that of the immediately preceding task program may be presented. If the correct response percentage is less than 50%, a program whose difficulty level is lower than that of the immediately preceding task program may be presented. In this case, it is necessary that the difficulty level is set for each task program.

The Noise-Vocoded Speech Sound may be displayed on the display device in characters when presented. For example, it is possible that a plurality of sentences, including the correct response and sentences confusingly similar to the correct response for hearing that are partially different from the correct response, are displayed, and the user inputs the number that the user believes to be the correct response to the response input section 15.

Selection of the bandpass filters of the bandpass filter sections 1 and 4, selection/switching of band frequency boundaries, and selection/switching by the automatic language recognition section described in Embodiment 2 may be applied to the present embodiment.

It should be noted that the response input section may be a touch panel or a mouse, etc., instead of a keyboard. In such a case, responses may be input by selecting characters from a table on which characters are indicated.

As described above, in this embodiment, the user can voluntarily carry out a menu for preventing senility using the above-described game-like apparatus for preventing senility.

Embodiment 4

Various game devices can be realized based on the configuration of FIG. 3 above. At first, a game title and difficulty level selection screen are displayed, after which the players select the difficulty level in the response input section 15, and the speech source selection control section 11 selects and presents Noise-Vocoded Speech Sound made up of words and sentences corresponding to the selected difficulty level. A record of correct response percentages, the number of correct responses, etc. are displayed on the display section 14 while the game is being played. When a high score is obtained, an entertaining screen may be displayed on the display section as a reward for the enjoyment of the players. A contest may be held to answer as many tasks as possible, and as correctly as possible, within a certain time. For such a game, a game device may be designed for people suffering from mild degree of dementia as well as for healthy people. The presented contents, the speed of presentation, and the presentation screens can be appropriately modified depending on the target audience. The desire to get a high score is expected to further stimulate brain activity.

The players may select the difficulty level of the game by operating the band selection section 12. For instance, they would select the number of the bandpass filters from 1 to 4 filters. Because in case of four filters the original words and sentences are distinguished more easily than in case of one filter, the players can select the difficulty level of the game.

Embodiment 5

Embodiments of the method for preventing senility of the present invention are explained below. FIG. 4 is an example of a flow chart illustrating a method used for implementing the functionality of the apparatus for preventing senility of the present invention.

During the speech input procedure (S10), an input speech signal obtained through the microphone of the apparatus for preventing senility is subjected to A/D conversion, preparing for passing of the speech data on to the bandpass filtering procedure (S12). The procedures described above are executed in a regular manner after this. Then, if necessary, the preset number of band frequencies and the boundary frequencies of band frequencies for bandpass filtering used in the subsequent bandpass filtering procedures (S12) and (S14) are adjusted and set during a band selection procedure (S11). This procedure is carried out if an operation by the user is involved. If no operation by the user is involved, this procedure is skipped. Next, during the bandpass filtering procedure (S12), the speech data is filtered based on the preset number of band frequencies and the boundary frequencies of band frequencies for bandpass filtering. During the envelope extraction procedure (S13), envelope component data is extracted from the filtered speech data. Next, during a bandpass filtering procedure (S14), a noise signal consisting of white noise is filtered using the preset number of band frequencies and the boundary frequencies of band frequencies for bandpass filtering, producing band noise signal data. The envelope component data and band noise signal data are multiplied together in the subsequent multiplication procedure (S15), and, if there are multiplication results for a plurality of bands, summed up in an addition procedure (S16). The summed speech data constitute Noise-Vocoded Speech Sound data. During the signal presentation procedure (S17), it is subjected to D/A conversion and presented to the user for listening through the earphones as an analog speech signal.

The procedures of (S10) to (S17) may be executed sequentially, as shown in FIG. 4, or carried out in parallel. These procedures can be implemented in the form of a software program for a digital signal processor (DSP).

In addition, the procedures of (S11) to (S16) constitute a Noise-Vocoded Speech Sound production procedure (S100).

It should be noted that the procedure of (S14) may be carried out prior to the procedures of (S12) and (S13).

In the band selection procedure (S11), the number of frequency bands and the boundary frequencies between frequency bands appropriate for the recognized language can be selected by providing an automatic language recognition procedure for Japanese, English, German, Chinese, etc. The technology of automatic language recognition is well-known, and detailed explanations are omitted herein.

Embodiment 6

FIG. 5 is an example of a flow chart of procedures for implementing a functionality of a game-like apparatus for preventing senility of the present invention.

When a program for preventing senility is started, during the speech source selection procedure (S20), predetermined words and sentences to be presented are selected from the speech source signal data, and provided to the Noise-Vocoded Speech Sound production procedure (S100). The Noise-Vocoded Speech Sound production procedure (S100) produces the Noise-Vocoded Speech Sound data. The produced Noise-Vocoded Speech Sound data is converted to an analog speech signal during the Noise-Vocoded Speech Sound presentation procedure (S21), and presented to the user for listening via headphones. During the response procedure (S22), the user tries to recognize the Noise-Vocoded Speech Sound presented for listening, and inputs words and sentences understood to the response input section 15. An evaluation device evaluates and determines whether the input response data is correct response during the response evaluation procedure (S23), and displays the result of correctness and the correct words and sentences to the display device during the correct response presentation procedure (S24). Then, a menu for preventing senility for one question ends. By repeating these procedures in series, one set of program menus for preventing senility that consists of a series of questions can be carries out.

Embodiment 7

Another embodiment of a method for preventing senility is described below. If the correct response percentage, correct response score or the like is displayed in the correct response presentation procedure (S24) in the procedures of the game-like apparatus for preventing senility of FIG. 5, procedures for preventing senility in the form of a game can be achieved.

Embodiment 8

In the apparatus for preventing senility of FIG. 1, an input speech signal from the microphone is applied to the bandpass filter section 1 through the input terminal 7. However, ambient noise components may sometimes be included in the input speech signal along with speech components. A configuration such as the one illustrated in FIG. 6 may be used in such a case. In FIG. 6, an input signal from the microphone applied to the input terminal 7 passes through a speech signal extraction section 9 and is then applied to the bandpass filter section 1. The speech signal extraction section 9 has the capability to extract a speech signal from an input speech signal comprising ambient noise etc. To this end, a configuration is used for the speech signal extraction section 9, in which noise components concomitant with the speech signal, which are contained in the input speech signal, are compressed using a technique such as spectral subtraction.

Embodiment 9

In the game-like apparatus for preventing senility of FIG. 2 and the game-like apparatus for preventing senility of FIG. 3, when ambient noise concomitant with speech components is contained in the speech signal of the speech source signal sections 10, the signal may be applied to the bandpass filter section 1 through the speech signal extraction section 9 described in FIG. 6. Moreover, in a game-like apparatus for preventing senility or a game device, in which one of two people inputs words and sentences through the microphone and another listens to Noise-Vocoded Speech Sound, trying to guess the original words and sentences, ambient noise may be mixed in, and therefore it is desirable to provide a speech signal extraction section 9.

Embodiment 10

FIG. 7 illustrates a configuration of a game-like apparatus for preventing senility based on the game-like apparatus for preventing senility of FIG. 3, in which a signal obtained by converting a speech signal into Noise-Vocoded Speech Sound is stored in the speech source signal section 10 of the game-like apparatus for preventing senility of FIG. 3 in advance, and the output signal thereof is presented to the user for listening through the headphones 13. The Noise-Vocoded Speech Sound signal is constituted by reading from the speech source signal section 10 the Noise-Vocoded Speech Sound signal stored therein, and output. Therefore, the bandpass filter sections 1 and 4, the envelop extraction section 2, the multiplication section 3, the noise source 5, the addition section 6 and the band selection section 12 of FIG. 3 may be eliminated. The same configuration may be applied to the game-like apparatus for preventing senility of FIG. 2.

Although in each of the embodiments described above, the number of the bandpass filters of the bandpass filter sections 1 and 4 was typically set to four, this number is not limited to four and may be less than four or greater than four, with the appropriate number of bands determined as the occasion demands.

Storing media on which the inventive software program documenting the procedure of the method for preventing senility of the present invention is stored, refers to storing media such as ROM, RAM, flexible disks, CD-ROMs, DVDs, memory cards, hard disks, etc., on which the software program is stored. Here, the software program of the procedure of the method for preventing senility is, for example, the one described below. Namely, this software program causes a computer to execute a first filtering step of extracting signals of a plurality of predetermined bands from a speech signal, an envelop extraction step of extracting the envelop of each frequency band signal extracted by the first filtering step, a second filtering step of extracting noise signal corresponding to the predetermined bands from the noise signal, a multiplying step of multiplying the signal extracted by the envelop extraction step and the signal extracted by the second filtering step, and an adding step of summing up the multiplied results of the multiplying step.

INDUSTRIAL APPLICABILITY

It is possible to activate various regions of brain with apparatuses and methods for preventing senility of the present invention, therefore, the apparatuses and methods for preventing senility can be used at training centers, care centers, medical institutions and the like for senior and elderly people. Since methods for preventing senility can be constructed with a software program and can be realized in a game form, installation on a terminal device such as a personnel information manager PDA, a mobile phone, a home PC, or an electrical household appliance, or the like is easy.

Figure 1:
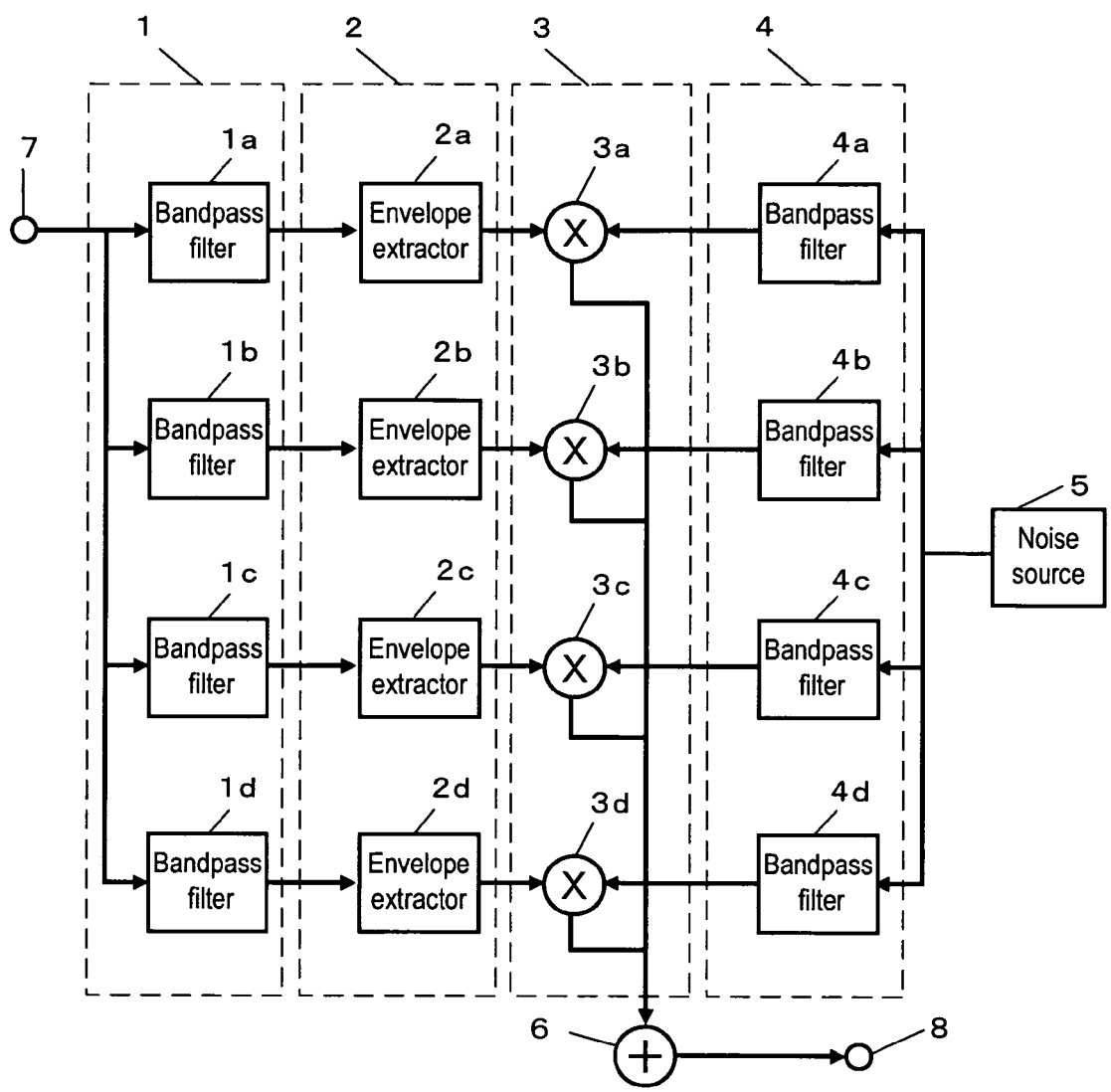
FIG. 1 is a block diagram of an apparatus for preventing senility according to an embodiment of the present invention.
Figure 2:
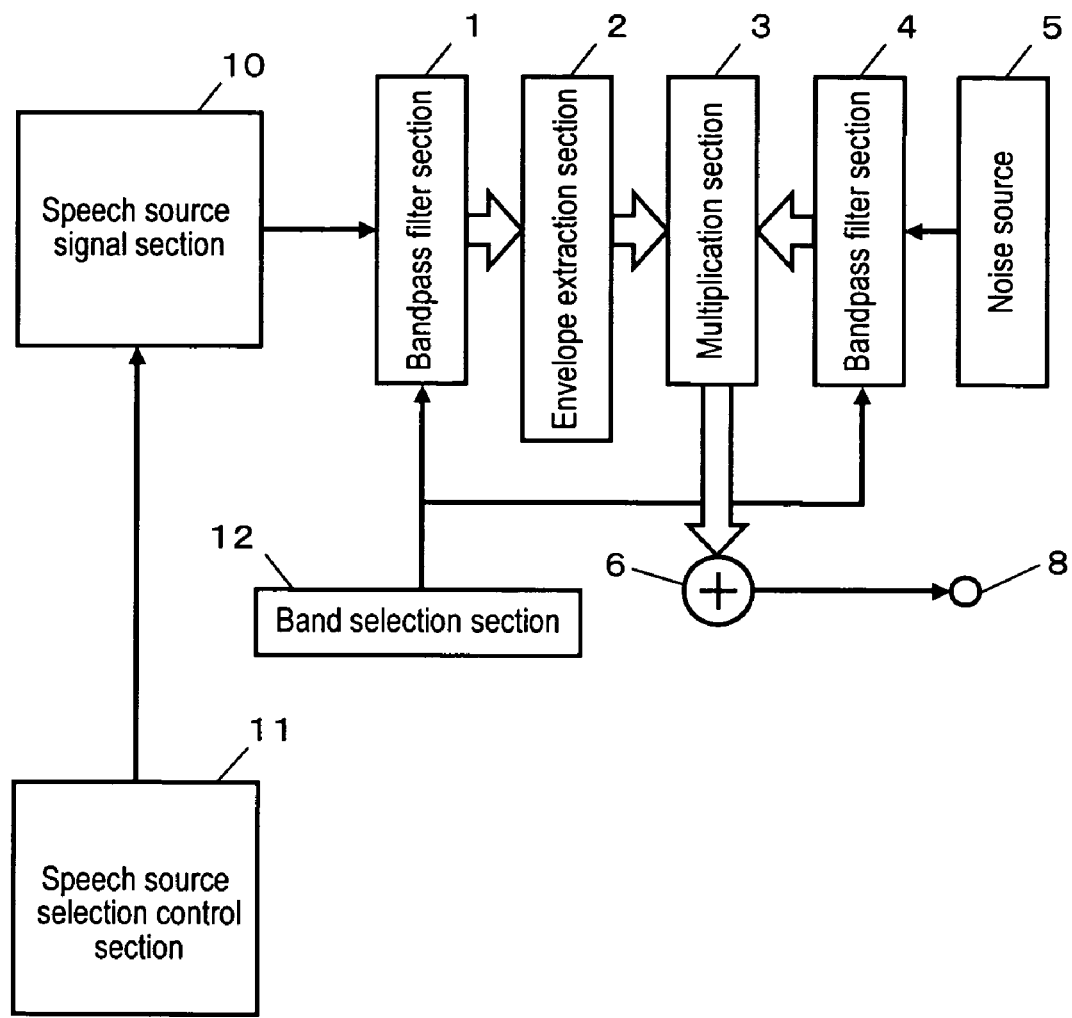
FIG. 2 is a block diagram of a game-like apparatus for preventing senility according to an embodiment of the present invention.
Figure 3:
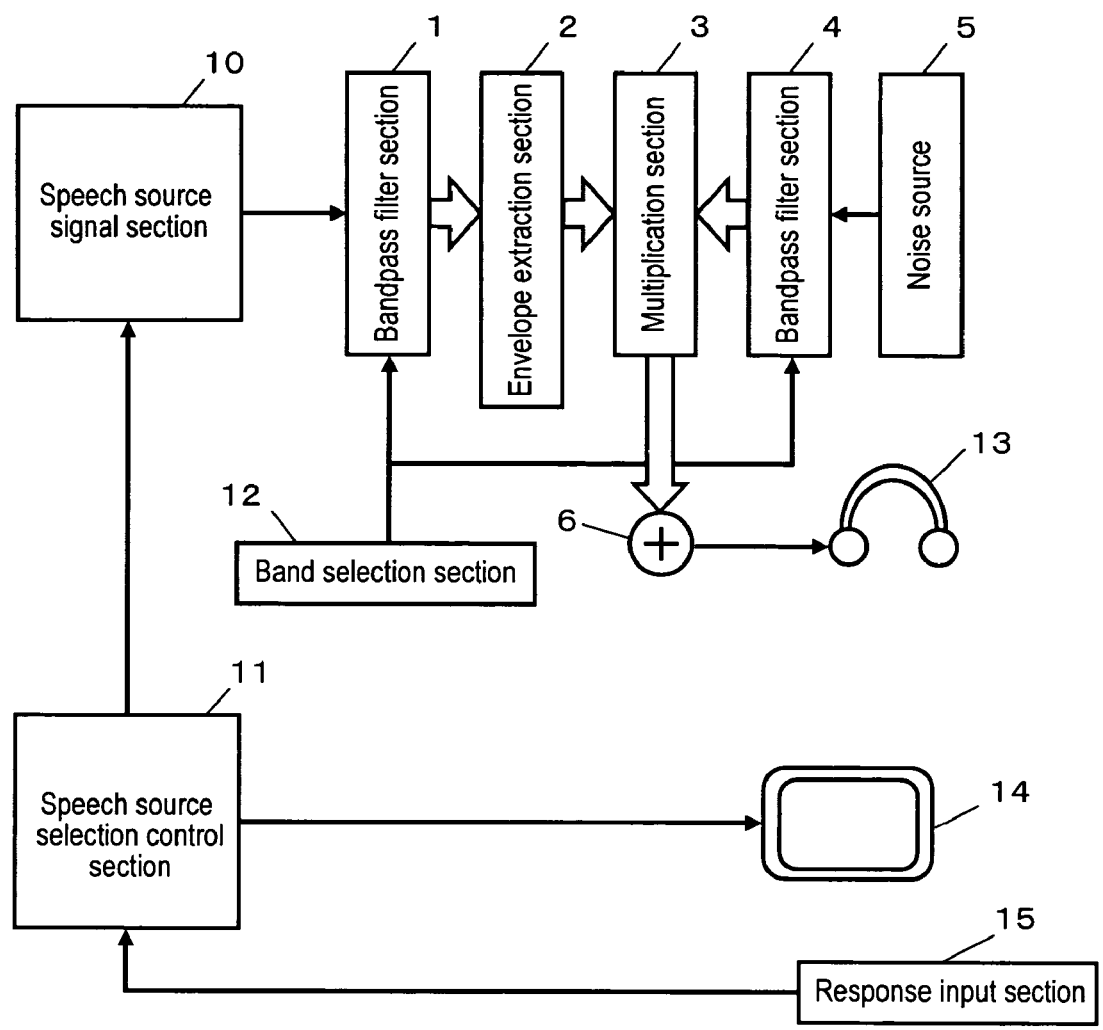
FIG. 3 is a block diagram of a game-like apparatus for preventing senility according to an embodiment of the present invention.
Figure 4:
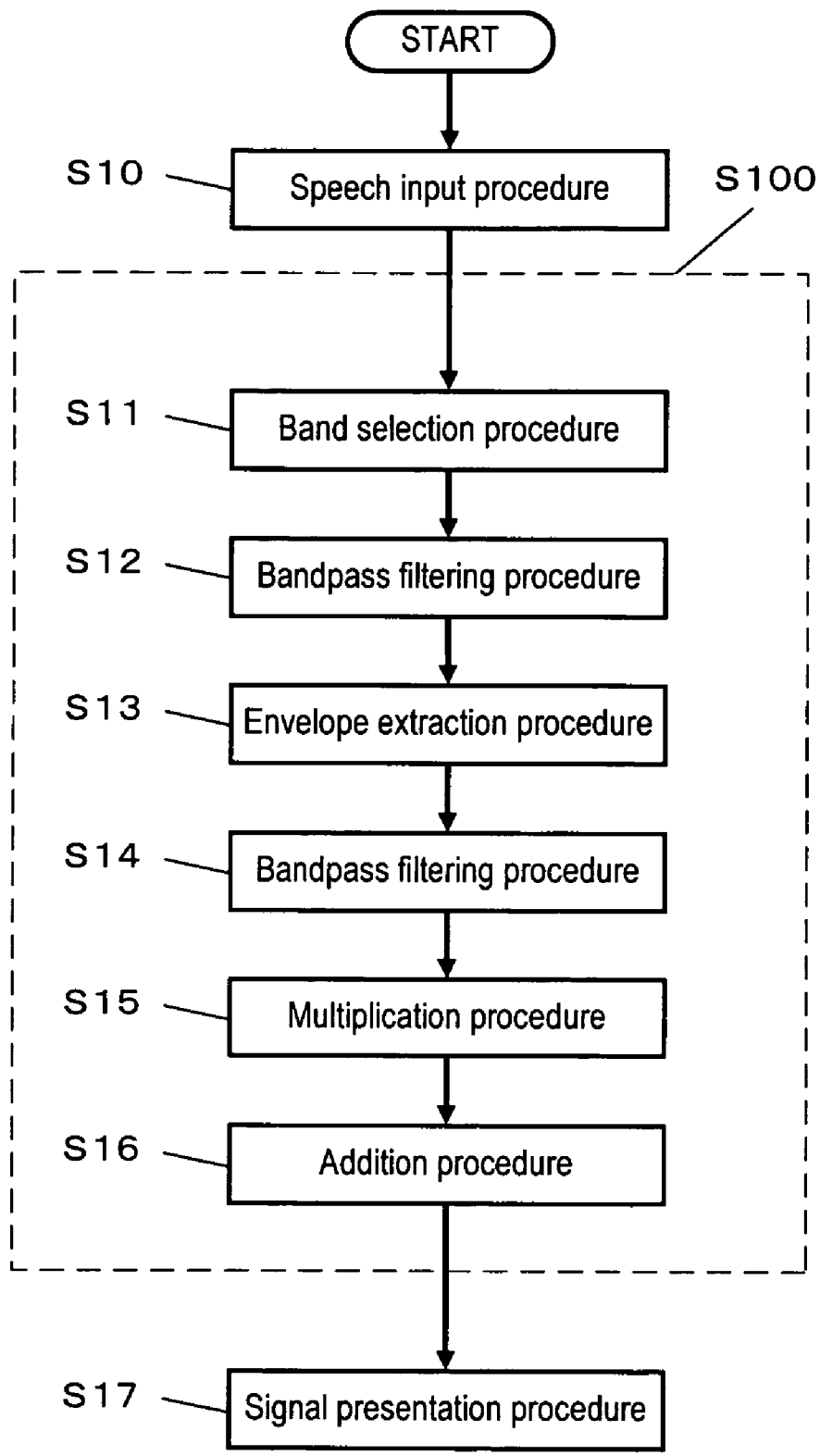
FIG. 4 is a flow chart illustrating the operation of an apparatus for preventing senility according to an embodiment of the present invention.
Figure 5:
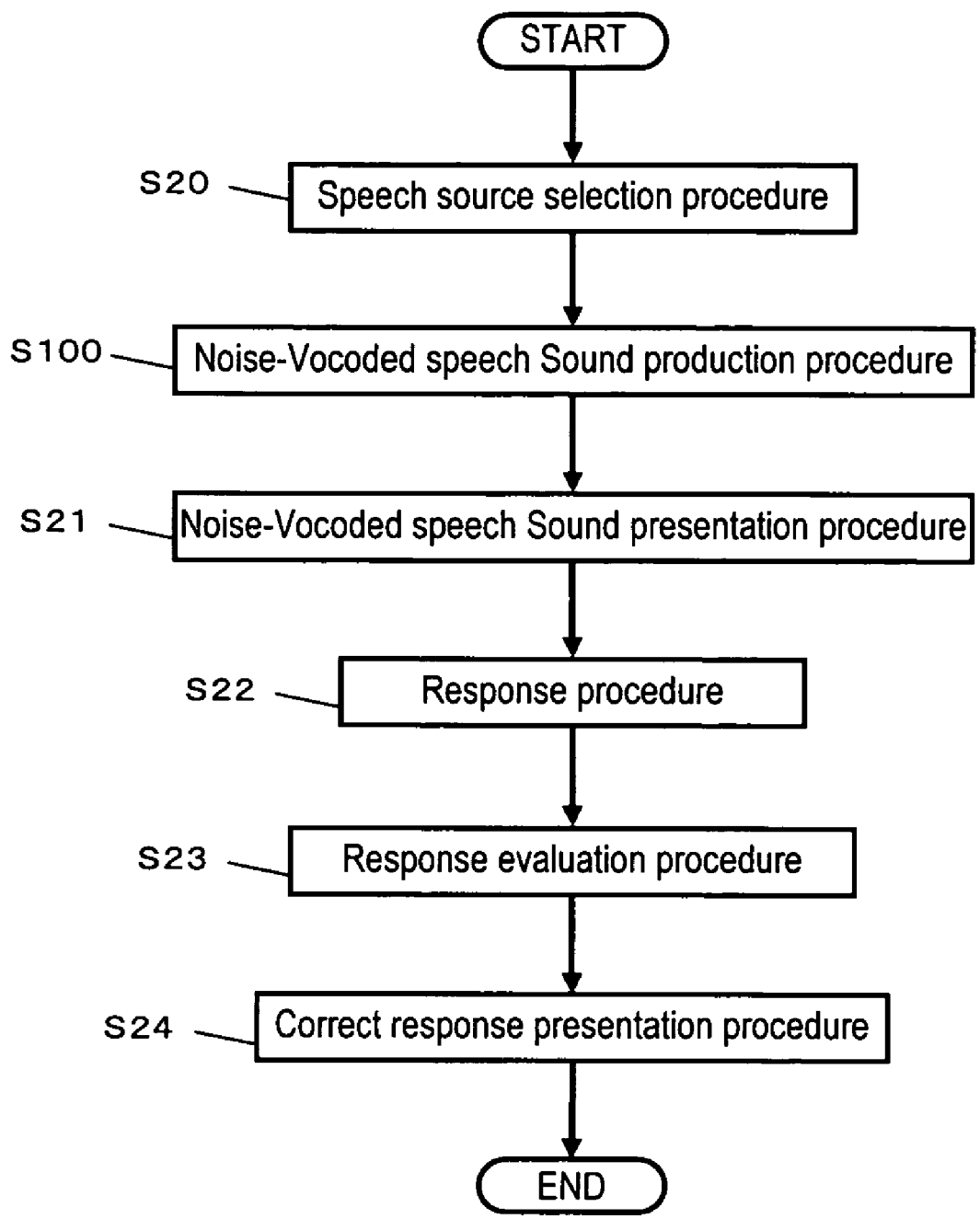
FIG. 5 is a flow chart illustrating the operation of a game-like apparatus for preventing senility according to an embodiment of the present invention.
Figure 6:
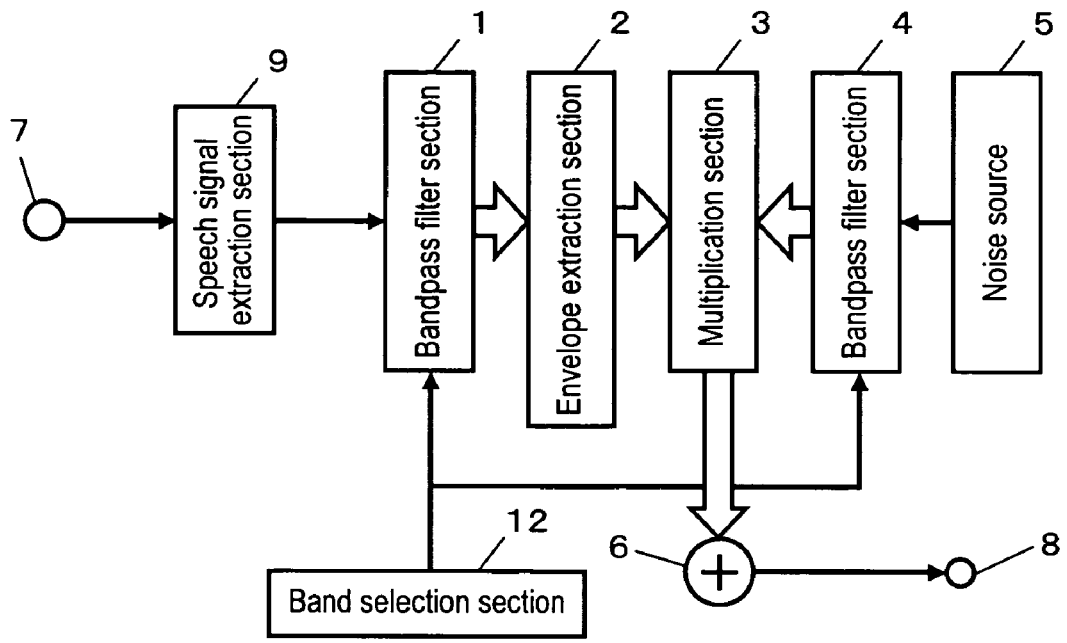
FIG. 6 is a block diagram of an apparatus for preventing senility according to an embodiment of the present invention.
Figure 7:
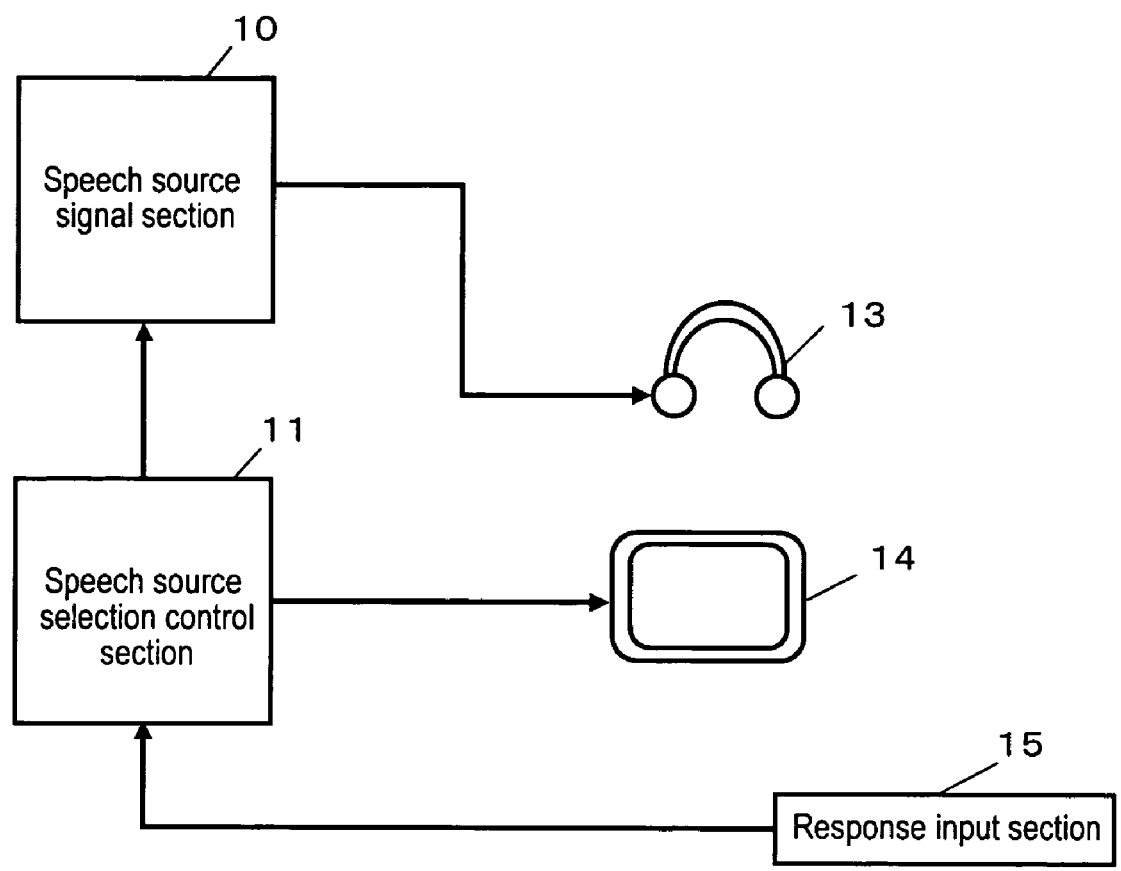
FIG. 7 is a block diagram of a game-like apparatus for preventing senility according to an embodiment of the present invention.
Figure 8:
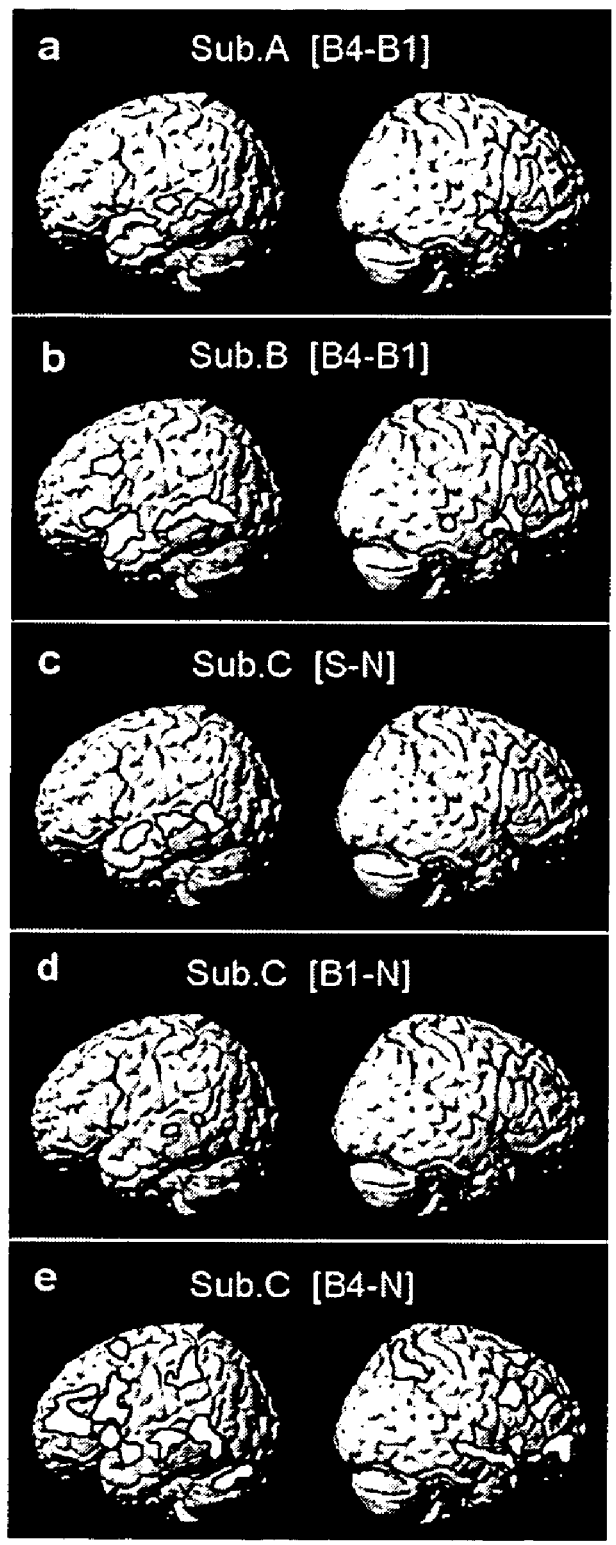
FIG. 8 is an observation example of activation of brain activity by Noise-Vocoded Speech Sound.

What is claimed is:

1. A method for preventing senility by constructing and applying a Noise-Vocoded Speech Sound signal comprising:
   dividing at least a portion of a speech signal into prescribed frequency band signals;
   extracting envelopes of each of the prescribed frequency band signals;
   subjecting each of the frequency band signals to noise degradation;
   summing up the outputs of the frequency band signals to form the Noise-Vocoded Speech Sound signal;
   outputting the Noise-Vocoded Speech Sound signal such that the Noise-Vocoded Speech Sound signal activates various brain regions other than typically activated brain regions during aural recognition.

2. A method for preventing senility by constructing and applying a Noise-Vocoded Speech Sound signal comprising steps of:
   extracting each of prescribed frequency band signals from a speech signal using a plurality of first bandpass filters of a first bandpass filter section;
   extracting each of envelopes of the frequency band signals using each of envelope extractors of an envelope extraction section;
   applying a noise source signal to a plurality of second bandpass filters of a second bandpass filter section;
   extracting noise signals corresponding to the plurality of prescribed frequency band signals;
   multiplying each of outputs from the envelop extraction section and each of outputs from the second bandpass filter section in a multiplication section;
   summing up the outputs from the multiplication section in an addition section to form the Noise-Vocoded Speech Sound signal; and
   outputting the Noise-Vocoded Speech Sound signal such that the Noise-Vocoded Speech Sound signal activates various brain regions other than typically activated brain regions during aural recognition.

3. The method for preventing senility according to claim 2, wherein at least one of the number of the first and second bandpass filters and the prescribed frequency of the first and second bandpass filters can be modified at least according to a language.

4. The method for preventing senility according to claim 2, wherein at least one of the number of the first and second bandpass filters and the prescribed frequency of the first and second bandpass filters can be modified through automatic language recognition.

5. The method for preventing senility according to claim 1 or 2, wherein only a speech component is extracted from the speech signal, and the Noise-Vocoded Speech Sound signal is produced from the extracted speech signal.

6. The method for preventing senility according to claim 1 or 2, wherein an output signal of a microphone is the speech signal.

7. The method for preventing senility according to claim 1 or 2, wherein the Noise-Vocoded Speech Sound signal is produced from a stored speech signal.

8. The method for preventing senility according to claim 1 or 2, further comprising:
   outputting the Noise-Vocoded Speech Sound signal to a user;
   accepting a user's response; and
   outputting correctness of the response.

* * * * *